| United States Patent [19] | [11] | 4,363,764 |
|---|---|---|
| Billig et al. | [45] | Dec. 14, 1982 |

[54] PREPARATION OF RHODIUM COMPLEX COMPOUNDS

[75] Inventors: Ernst Billig, Charleston; David R. Bryant, South Charleston; Jackie D. Jamerson, Charleston, all of W. Va.

[73] Assignee: Union Carbide Corporation, Danbury, Conn.

[21] Appl. No.: 221,502

[22] Filed: Dec. 30, 1980

[51] Int. Cl.$^3$ .............................................. C07F 15/00
[52] U.S. Cl. ................................................ 260/429 R
[58] Field of Search .................................... 260/429 R

[56] References Cited

U.S. PATENT DOCUMENTS

| 3,560,539 | 2/1971 | Booth | 260/429 |
|---|---|---|---|
| 3,641,076 | 2/1972 | Booth | 260/429 R |
| 3,644,446 | 2/1972 | Booth et al. | 260/429 R |
| 3,857,895 | 12/1974 | Booth | 260/604 HF |
| 3,859,359 | 1/1975 | Keblys | 260/604 HF |
| 3,968,134 | 7/1976 | Gregorio | 260/429 R |
| 4,021,463 | 5/1977 | Kummer et al. | 260/429 R |
| 4,113,754 | 9/1978 | Kummer et al. | 260/429 R |
| 4,277,414 | 7/1981 | Saito et al. | 260/429 R |

OTHER PUBLICATIONS

N. Ahmad et al., *Inorganic Synthesis*, vol. XV, (1974) Chapter 3, pp. 45 to 47, 59 and 60.
D. Evans et al., *J. Chem. Soc.*(A), (1968), pp. 2660 to 2665.
Gregorio et al. *Inorg. Chem. Acta* vol. 3, No. 1, (1969), pp. 89 to 93.
Varshaski et al., *Russian Journal of Inorganic Chemistry*, vol. 12, No. 6, Jun. 1967, p. 899.

*Primary Examiner*—Helen M. S. Sneed
*Attorney, Agent, or Firm*—Reynold J. Finnegan

[57] ABSTRACT

Process for preparing halocarbonylbis(triorganophosphorus) rhodium compounds and hydridocarbonyltris(triorganophosphorus) rhodium compounds.

20 Claims, No Drawings

PREPARATION OF RHODIUM COMPLEX COMPOUNDS

BACKGROUND OF THE INVENTION

This invention relates to a process for preparing halocarbonylbis(triorganophosphorus) rhodium compounds and to a process for preparing hydridocarbonyltris(triorganophosphorus) rhodium compounds directly from said halocarbonylbis(triorganophosphorus) rhodium compounds. More particularly this invention relates to an organic one-phase process for preparing halocarbonylbis(triorganophosphorus) rhodium compounds from an organic concentrate of a spent hydroformylation reaction medium and to a process for preparing hydridocarbonyltris(triorganophosphorus) rhodium compounds directly from said halocarbonylbis(triorganophosphorus) rhodium compounds so produced without isolating such halo-containing rhodium compounds from their product mixture.

Organic one-phase processes for preparing halocarbonylbis(triorganophosphorus) rhodium compounds from simple rhodium chloride monomeric compounds are known in the art, e.g. J. A. McCleverty et al. "Inorganic Syntheses", Vol. 8, page 214 (1966) and D. Evans et al. "Inorganic Syntheses", Vol. XI. pp. 99 to 101 (1968) disclose reacting rhodium trichlorohydrate ($RhCl_3.3H_2O$) with formaldehyde and triphenylphosphine in the presence of an organic solvent to produce chlorocarbonylbis(triphenylphosphine) rhodium. However, methods for preparing halocarbonylbis(triorganophosphorus) rhodium compounds from distillation residues of rhodium catalyzed hydroformylation processes are much more difficult and heretofore have involved aqueous phase type transfer processes wherein the reaction is conducted in the presence of an aqueous solution.

For example U.S. Pat. No. 4,021,463 discloses a process for preparing halocarbonylbis(triorganophosphine) rhodium by treating the distillation residue of a hydroformylation mixture with an aqueous mineral acid and a peroxide to convert the rhodium into its water-soluble salt which passes into the aqueous phase, mixing the resulting aqueous salt solution with a solvent, tertiary phosphine and hydrohalic acid or metal halide and reacting the aqueous solution with carbon monoxide or a carbon monoxide donor. Said patent further discloses that hydridocarbonyltris(triorganophosphine) rhodium can be produced by simultaneously subjecting the aqueous starting solution to hydrogenation conditions or by subjecting a solvent solution of the halo-containing compound product together with additional phosphine to hydrogenation conditions.

U.S. Pat. No. 4,113,754 discloses a process for preparing chlorocarbonylbis(triorganophosphine) rhodium compounds by treating a distillation residue of a hydroformylation mixture with oxygen containing mineral acids and peroxides to form an aqueous rhodium salt solution which is then treated with a cation exchanger and the latter separated from the solution. The absorbed rhodium ions are deabsorbed with hydrochloric acid and the hexachlororhodate solution containing HCl then reacted in the presence of a water-soluble organic solvent, a tertiary phoshine and carbon monoxide to produce the desired product. The patent further discloses that if the process is carried out under hydrogenation conditions that hydridocarbonyltris(triorganophosphine) rhodium is produced.

U.S. Pat. No. 3,968,134 discloses a process for preparing chlorocarbonylbis(triorganophosphine) rhodium compounds by treating a raw hydroformylation product, or the tails of a distillation of same containing a triorganophosphine ligand with an aqueous solution of an aldehyde and a strong acid (e.g. HCl), obtaining the desired rhodium product by filtration and separating the aqueous solution containing triorganophosphine by decantation.

SUMMARY OF THE INVENTION

It has now been discovered that halocarbonylbis(triorganophosphorus) rhodium compounds can be prepared by an organic one-phase process that is especially suitable for recovering the spent rhodium values of large scale commercial hydroformylation operations by converting the spent rhodium of such operations into high yields of said halocarbonylbis(triorganophosphorus) rhodium compounds and that hydridocarbonyltris(triorganophosphorus) rhodium compounds can be prepared directly from said halocarbonylbis(triorganophosphorus) rhodium compounds without having to isolate such halo-containing rhodium compounds from their product mixture.

Thus it is an object of this invention to provide both a process for preparing halocarbonylbis(triorganophosphorus) rhodium compounds and a process for preparing hydridocarbonyltris(triorganophosphorus) rhodium compounds. It is another object of this invention to provide an organic one-phase process for preparing said halocarbonylbis(triorganophosphorus) rhodium compounds from an organic concentrate of a spent hydroformylation reaction medium. It is a further object of this invention to provide a process for preparing hydridocarbonyltris(triorganophosphorus) rhodium compounds directly from said halocarbonylbis(triorganophosphorus) rhodium compounds so produced without isolating said halocarbonylbis(triorganophosphorus) rhodium compounds from their product mixture. Other objects and advantages of this invention will become readily apparent from the following written description and appended claims.

Accordingly a generic aspect of this invention can be described as an organic one-phase process for preparing a halocarbonylbis(triorganophosphorus) rhodium compound which comprises reacting, at a temperature from about 40° C. to about 200° C., an essentially non-aqueous, homogeneous organic reaction solution consisting essentially of (a) a rhodium complex concentrate, (b) a halide ion source, (c) carbon monoxide gas or a carbon monoxide source and (d) free triorganophosphorus ligand, for at least a sufficient period of time to form said halocarbonylbis(triorganophosphorus) rhodium compound; said rhodium complex concentrate consisting essentially of from about 0.1 to about 30 percent by weight of a spent hydroformylation reaction medium and having been produced by concentrating a spent hydroformylation reaction medium that contains a partially deactivated soluble rhodium complex hydroformylation catalyst, aldehyde products, higher boiling aldehyde condensation by products and free triorganophosphorus ligand, so as to remove from said medium, while retaining a major amount of the rhodium values of said catalyst present in said medium, at least essentially all of said aldehyde products, at least 50 percent by weight of said higher boiling aldehyde condensation by-products that have a boiling point below that of said free triorganophosphorus ligand present in said medium and at least 50 percent by weight of said free triorganophosphorus ligand present in said medium.

Another generic aspect of this invention can be described as a process for preparing a hydridocarbonyltris(triorganophosphorus) rhodium compound which comprises reacting, at a temperature of from about 20° C. to about 100° C., the halocarbonylbis(triorganophosphorus) rhodium compound produced according to this invention without isolating said halocarbonylbis(triorganophosphorus) rhodium compound from its product mixture, with a metal hydride reducing agent and free triorganophosphorus ligand, for at least a sufficient period of time to form said hydridocarbonyltris(triorganophosphorus) compound.

DESCRIPTION OF THE PREFERRED EMBODIMENTS

As seen discussed above one of the points of novelty of this invention rests in the discovery that a rhodium complex concentrate of a spent hydroformylation reaction medium can be employed as the starting material of this invention. Such rhodium complex concentrates consist essentially of from 0.1 to about 30 percent by weight of a spent hydroformylation reaction medium and are produced by concentrating said medium to said desired rhodium complex concentrate. More preferably the rhodium complex concentrate consists essentially of from about 1 to about 10 percent by weight, and most preferably from about 2 to about 6 percent by weight of the spent hydroformylation reaction medium.

The term "spent hydroformylation reaction medium" as employed herein means any hydroformylation reaction medium, or any part thereof, containing a rhodium complex hydroformylation catalyst, aldehyde products, higher boiling aldehyde condensation by-products and free triorganophosphorus ligand that has been employed in any process directed to producing aldehydes by hydroformylating an olefinic compound with carbon monoxide and hydrogen and which process has been operated to the extent that said catalyst has become at least partially deactivated. Thus the particular hydroformylation process and reaction conditions for producing aldehydes from which the spent hydroformylation reaction medium is derived are not narrowly critical features of the present invention, since such serves only as a means of supplying the spent hydroformylation reaction medium to be concentrated to the rhodium complex concentrate starting material of this invention. Thus while the spent hydroformylation mediums concentrated according to this invention may be derived from any suitable hydroformylation process, such as disclosed e.g. in U.S. Pat. No. 3,527,809 and the article "Industrialization of Rhodium Process Oxo Reaction Technology" by Yamaguchi in *Nikkakyo Gepto*, Vol. 32, No. 3, pp. 14–22 (1979), the preferred spent hydroformylation reaction mediums are derived from continuous hydroformylation procedures such as taught e.g. in U.S. Pat. No. 4,148,830 and U.S. application Ser. Nos. 776,934 filed Mar. 11, 1977 (now U.S. Pat. No. 4,247,486) and 190,280 filed Sept. 24, 1980, the disclosures of which are incorporated herein by reference thereto. Moreover, in general it is preferred to concentrate those spent hydroformylation reaction mediums in which the rhodium complex catalyst has become at least 60 percent deactivated and more preferably that has become so deactivated that it is no longer economical to continue the hydroformylation process. However, it is not necessary to await such an event, since the rhodium complex concentrate of this invention can be derived from any such spent hydroformylation reaction medium which contains at least a partially deactivated rhodium hydroformylation catalyst, i.e. a catalyst which is less active than its original counterpart. The extent of deactivation of the catalyst may be determined at any given time during the hydroformylation reaction, e.g. by comparing the conversion rate to product based on such catalyst to the conversion rate obtained using fresh catalyst.

Thus the spent hydroformylation reaction mediums employable in this invention are those that contain a partially deactivated rhodium complex catalyst, aldehyde products, higher boiling aldehyde condensation by-products and free triorganophosphorus ligand and can contain additional ingredients which have either been deliberately added to the reaction medium of the hydroformylation process or formed in situ during said process.

Accordingly the partially deactivated rhodium complex hydroformylation catalyst, present in the spent hydroformylation reaction medium to be concentrated according to this invention can be any rhodium hydroformylation catalyst suitable for use in a hydroformylation reaction and which has been employed in a hydroformylation reaction to the extent that it has become partially deactivated i.e. does not have the same rate of activity of corresponding fresh rhodium complex catalyst.

Thus the particular partially deactivated rhodium complex hydroformylation catalyst, as well as its amount, present in a given spent hydroformylation reaction medium to be concentrated will obviously correspond to and merely be dependent upon the particular rhodium complex hydroformylation catalyst employed in and/or formed under the reaction conditions of the hydroformylation reaction from whence the spent hydroformylation reaction medium to be concentrated has been derived. In general such rhodium complex hydroformylation catalysts comprise rhodium complexed with a triorganophosphorus ligand. For example, as seen by the preferred operational features taught in U.S. Pat. Nos. 3,527,809 and 4,148,830 and said Ser. No. 776,934, the preferred hydroformylation reaction mediums contain a rhodium complex catalyst consisting essentially of rhodium complexed with carbon monoxide and triarylphosphine (corresponding to the free triarylphosphine ligand also contained in said medium). As such hydroformylation reactions continue, alkyl substituted phosphine is formed in situ, the amount of which continues to build up over the period of time that a continuous hydroformylation reaction is operational. Said alkyl substituted phosphine ligand having a greater affinity for rhodium than triarylphosphine may also tie or bind itself to the rhodium thereby resulting in a rhodium complexed catalyst consisting essentially of rhodium complexed with carbon monoxide, triarylphosphine ligand and/or said alkyl substituted phosphine ligand (i.e. either one or both of said triarylphosphine ligand and said alkyl substituted phosphine ligand). Thus, it is to be understood that the rhodium complex catalyst terminology "consisting essentially of", as employed herein, is not meant to exclude, but rather include the likely possibility of alkyl substituted phosphine and hydrogen complexed with the rhodium in addition to carbon monoxide and triarylphosphine, the hydrogen being derived from the hydrogen gas of the hydroformylation reaction if not already present in the catalyst precursor.

As pointed out in the above discussed prior art the rhodium complex hydroformylation complex catalyst may be formed in situ during the hydroformylation reaction or preformed by methods known in the art. Thus it is not intended to limit the present invention by any explanation as to the exact nature of the active rhodium complex hydroformylation catalyst or to the nature of the deactivated rhodium hydroformylation catalyst formed during the hydroformylation reaction. Clearly it is sufficient for the purpose of this invention to simply point out that carbon monoxide, triorganophosphorus compounds and hydrogen are all ligands that are capable of being complexed with the rhodium to form both the active and/or partially deactivated rhodium complex catalyst of a hydroformylation reaction.

Accordingly, in general the amount of partially deactivated rhodium complex hydroformylation catalyst present in the spent hydroformylation reaction medium to be concentrated according to this invention will correspond to that catalytic amount of rhodium catalyst present in the hydroformylation reaction from whence said medium to be concentrated has been derived, and may be that amount sufficient to provide a rhodium concentration in said medium to be concentrated which may range from about 25 ppm to about 1200 ppm and preferably from about 50 ppm to about 600 ppm of rhodium calculated as free metal.

The particular aldehyde products present in a given spent hydroformylation reaction medium to be concentrated according to this invention will obviously correspond to those aldehyde products produced by the particular hydroformylation reaction from whence the spent hydroformylation reaction medium to be concentrated has been derived. Preferably such aldehyde products are mixtures rich in their normal isomers, i.e., contain at least about four moles of normal aldehyde product per mole of isomeric aldehyde product. For example, the continuous hydroformylation of propylene produces butyraldehyde products, which products under preferred operational conditions are rich in normal butyraldehyde. Of course, the particular aldehyde products contained in a given spent hydroformylation reaction medium to be concentrated will also depend upon the particular olefinic compound employed in the hydroformylation reaction from whence said medium to be concentrated is derived. Said aldehyde products, of course, each contain one more carbon atom than the olefinic compound employed in the hydroformylation reaction. Olefinic compounds that may be employed in such hydroformylation reactions include those containing from 2 to 20 carbon atoms and which may contain groups or substitutes that do not essentially interfere with the course of the hydroformylation reaction and the process of this invention, such as generically taught in the prior art, especially U.S. Pat. No. 3,527,809. Illustrative olefinic compounds include alkenes such as alpha olefins and internal olefins, alkyl alkenoates, alkenyl alkanoates, alkenyl alkylethers, alkenols and the like. The preferred olefinic compounds are alpha-olefins containing from 2 to 20 carbon atoms and more preferably from 2 to 6 carbon atoms, such as ethylene, propylene, 1-butylene, 1-pentylene, 1-hexylene, and the like.

Thus the spent hydroformylation reaction medium to be concentrated according to this invention will also contain at least some portion of the aldehyde products produced by the particular hydroformylation reaction involved from whence said spent mediums are derived. In general the amount of aldehyde products present in the spent hydroformylation reaction medium to be concentrated according to this invention may range from about 1.0 to about 80 percent by weight and more preferably from about 10 to about 60 percent by weight, based on the total weight of said spent hydroformylation reaction medium to be concentrated.

As is known in the prior art, during such hydroformylation reactions a substantial amount of higher boiling aldehyde condensation by-products is formed in situ and is preferably retained in the hydroformylation reaction medium of the reaction to serve as a solvent for the rhodium complex hydroformylation catalyst as fully explained in said U.S. Pat. No. 4,148,830 and said Ser. No. 776,934. Moreover, in general the major amount of such higher boiling aldehyde condensation by-products are liquid condensation by-products having a boiling point below that of the free triorganophosphorus ligand present in the hydroformylation reaction medium, while a minor amount of such higher boiling aldehyde condensation by-products are those liquid condensation by-products having a boiling point above that of the free triorganophosphorus ligand present in the hydroformylation reaction medium. For example, in the continuous hydroformylation of propylene to produce butyraldehyde in the presence of free triphenylphosphine ligand the higher boiling aldehyde condensation by-products generally comprise a major amount of various trimer and tetramer aldehyde condensation by-products that have a boiling point below that of said free triphenylphosphine ligand and a minor amount of pentamer aldehyde condensation by-products and the like that have a boiling point above that of said free triphenylphosphine ligand. Thus it is to be understood that the term "higher boiling aldehyde condensation by-products" as employed herein, unless otherwise specifically designated, includes mixtures of both such types of by-products, i.e. those having a boiling point below that of the free triorganophosphorus ligand present in the hydroformylation reaction medium and those having a boiling point above that of the free triorganophosphorus ligand present in the hydroformylation reaction medium. Accordingly the particular higher boiling aldehyde condensation by-products, as well as their total amount, present in a given spent hydroformylation reaction medium to be concentrated according to this invention will generally correspond to those higher boiling aldehyde condensation by-products retained in the hydroformylation reaction medium and formed in situ during the particular hydroformylation reaction from whence the spent hydroformylation reaction medium to be concentrated has been derived. In general the total amount of higher boiling aldehyde condensation by-products present in the hydroformylation medium to be concentrated according to this invention may range from about 5 to about 95 percent by weight and more preferably ranges from about 50 to about 90 percent by weight, based on the total weight of said medium to be concentrated.

The free triorganophosphorus ligand i.e. that amount of triorganophosphorus ligand that is not complexed with or tied to the rhodium complex hydroformylation reaction catalyst as well as the triorganophosphorus ligand complexed with the rhodium complex hydroformylation catalyst present in the spent hydroformylation reaction medium to be concentrated according to this invention will obviously correspond to those particular phosphorus ligands employed in the particular hydroformylation reaction from whence the spent hydroformylation reaction medium to be concentrated has been derived and thus can be any triorganophosphorus ligand suitable for such hydroformylation reaction technology. Such triorganophosphorus ligands are well known in the art as seen by the above discussed references, the more common ligands being triorganophosphites and triorganophosphines. Triorganophosphine ligands are presently preferred, especially triarylphosphines, the most preferred ligand being triphenylphosphine. In general the amount of free triorganophosphorus ligand present in the spent hydroformylation reaction medium to be concentrated according to this invention may range from about 1 percent by weight to about 25 percent by weight and more preferably from about 5 percent by weight to about 20 percent by weight, based on the total weight of said medium to be concentrated. Moreover, in preferred continuous hydroformylation reactions particularly advantageous results are achieved when the amount of free triorganphosorus ligand in the hydroformylation reaction medium of such reactions is at least about 100 moles of free triorganophosphorus ligand per mole of catalytically active rhodium metal present in the rhodium complex hydroformylation catalyst. Thus the preferred hydroformylation reaction medium to be concentrated according to this invention will also generally contain at least about 100 moles of free triorganophosphorus ligand per mole of catalytically active rhodium metal present in the rhodium complex hydroformylation catalyst of said medium to be concentrated.

Moreover such spent hydroformylation mediums to be concentrated may also contain in conventional amounts, additional ingredients deliberately added to or formed in situ during the hydroformylation process from whence said spent mediums are derived. For example, such hydroformylation processes may be conducted in the presence of any additional suitable organic solvent, e.g., such as disclosed and described in U.S. Pat. No. 3,527,809. Further such spent hydroformylation reaction mediums may contain other triorganophosphorus ligands that are different from the main free triorganophosphorus ligand present in the reaction medium of the hydroformylation process as a result of deliberate addition or in situ formation. For instance, U.S. application Ser. No. 762,335 filed Jan. 25, 1977 (Belgium Pat. No. 863,267) now U.S. Pat. No. 4,260,828, the entire disclosure of which is incorporated herein by reference thereto, discloses that the stability of the rhodium complex catalyst can be enhanced by the presence of an alkyldiarylphosphine which may be deliberately added to the reaction medium of the hydroformylation process or formed in situ. For example the continuous hydroformylation of propylene in the presence of free triphenylphosphine ligand results in the in situ production of propyldiphenylphosphine. Likewise such spent hydroformylation reaction mediums may also obviously contain some unreacted olefinic starting materials and in addition may further contain organophosphorus oxides which correspond to the organophosphorus ligands present in the reaction medium of the hydroformylation process, which oxides may be the result of in situ formation during the process due to adventitious oxygen or as the result of a deliberate oxidative treatment of the reaction medium of the process, e.g. as disclosed in U.S. Pat. No. 4,221,743 and said Ser. No. 190,280.

The rhodium complex concentrate employable in this invention can be produced by any conventional method or combination of methods which comprises forming a rhodium complex concentrate consisting essentially of from about 0.1 to about 30 percent by weight by concentrating a spent hydroformylation reaction medium as defined above so as to remove, while retaining a major amount of the rhodium values of the partially deactivated rhodium complex catalyst present in said medium, at least essentially all of the aldehyde products present in said medium, at least 50 percent by weight of the higher boiling aldehyde condensation by-products present in said medium that have a boiling point below that of the free triorganophosphorus ligand present in said medium, and at least 50 percent by weight of the free triorganophosphorus ligand present in said medium.

For example, it is generally preferred to concentrate the spent hydroformylation reaction medium by means of distillation as taught in U.S. application Ser. No. 120,101, filed Feb. 28, 1980, now U.S. Pat. No. 4,297,239, the entire disclosure of which is incorporated herein by reference thereto. Such a procedure involves concentrating the spent hydroformylation reaction medium into at least two material streams by means of distillation at temperatures of about 20° to about 350° C. and at pressures of about 1000 to about $1 \times 10^{-6}$ mm. Hg., wherein one stream is said rhodium complex concentrate (i.e. the distillation residue) containing a major amount of the rhodium values of the partially deactivated rhodium hydroformylation catalyst present in said medium and which has been concentrated to about 0.1 to about 30 percent by weight of said spent hydroformylation reaction medium, and the other material stream or streams consist essentially of one or more of the distilled volatiles of said spent hydroformylation reaction medium, i.e. the aldehyde products, higher boiling aldehyde condensation by-products having a boiling point below that of the free triorganophosphorus ligand present in said medium, and the free triorganophosphorus ligand of said medium.

The distillation procedure preferably takes place in two stages, the first stage being conducted at temperatures of about 20° to 250° C., preferably from 20° to 190° C., and pressures of about 1000 to about 0.1 mm Hg., preferably about 150 to 0.5 mm Hg., which may effect up to about a threefold concentration of the spent hydroformylation reaction medium; the second stage of the distillation being conducted at temperatures of about 25° to 350° C., preferably from about 150° to about 300° C., and pressures of about 100 to $1 \times 10^{-6}$ mm Hg., preferably about 20 to 0.1 mm Hg., so as to further concentrate the bottom or residue product of the first stage to the finally desired rhodium complex concentrate which may contain from about 1000 to about 70,000 ppm, more preferably from about 1500 to about 15,000 ppm, and most preferably from about 2,000 to 12,000 ppm, of rhodium calculated as free metal.

The first distillation stage is employed to distill off and remove the most volatile components, e.g. the aldehyde products, that are present in the spent hydroformylation medium since such low boiling volatile components interfere with obtaining the desired low pressures employed in the second distillation stage and needed for the most effective removal of the less volatile (i.e. higher boiling) components and said free triorganophosphorus ligand present in said medium.

The second distillation stage involves taking the liquid residue or bottoms of said first distillation stage containing the partially deactivated rhodium complex catalyst and less volatile components, such as said higher boiling aldehyde condensation by-products and the free triorganophosphorus ligands of the spent hydroformylation reaction medium, and subjecting it to further distillation at the reduced pressures given above so as to distill off and remove free triorganophosphorus ligand and the higher boiling aldehyde condensation by-products that have a boiling point above said aldehyde products but below that of the free triorganophosphorus ligand present in said residue. The desired rhodium complex concentrate employable in this invention is thus recovered as the distillation residue of said second stage distillation and contains a major amount of the rhodium values of said partially deactivated catalyst (i.e. more than 50 percent by weight, preferably more than 90 percent by weight, of the total amount of rhodium values of said catalyst). For obvious economic reasons it is most desirable that the rhodium complex concentrate contain essentially (i.e. greater than 97 percent by weight) all of the rhodium values of said partially deactivated catalyst.

The distillation of each separation stage can be carried out by using any suitable distillation system and can take place on a continuous and/or discontinuous (batch) basis. However, care should be taken to avoid overheating the rhodium complex. It is also important to maintain a high vacuum in the second distillation stage so that the temperature required for concentration can be minimized. Thus the distillation is preferably carried out at the lowest temperature and shortest residence time required to achieve the desired rhodium concentration. Accordingly it is preferred to employ a thin-film evaporator, such as a wiped-film evaporator, since in such systems residence times at elevated temperatures of less than 10 minutes should be suitable in most instances, and preferably such residence times will be less than about three minutes, whereas in a kettle-type batch distillation the residence time for the second stage of distillation can be hours. However, batch systems are readily suitable for the first stage of distillation, since such is concerned with only removing the most volatile (lower boiling) components of the spent medium and thus the distillation can be carried out at rather mild temperatures and at much higher pressures than those pressures employed in the second distillation stage. In general, it is preferred to carry out both distillation stages in a thin-film evaporator, especially a wiped-film evaporator. Such evaporators are well known in the art and thus need not be further discussed herein. Of course, it is also to be understood that the procedure of each distillation stage can be carried out more than once, i.e., repeated until the desired amount of volatiles have been removed and/or the desired rhodium concentration obtained.

It should be noted that a fundamental change in the rhodium species present in the partially deactivated catalyst occurs during the distillation concentration procedure. The rhodium species found in the rhodium complex concentrates produced by the distillation concentration procedure are different in that it is generally larger in size than those species found in partially deactivated rhodium complex catalysts. Said rhodium complex concentrates so obtained have a dark brownish color and are highly viscous rhodium complex mediums.

Moreover, adding an oxidant such as oxygen and/or an organic peroxide to the rhodium complex concentrates employable in this invention can lead to an increase in the yield of desired halocarbonylbis(triorganophosphorus) rhodium compound prepared according to this invention.

It is difficult to ascertain the precise reasons for such an improvement in the yield of the halocarbonylbis(triorganophosphorus) rhodium compound produced according to this invention when the rhodium complex concentrate is contacted with an oxidant. However, it is believed that the oxidant, for whatever reason, somehow renders the large rhodium clusters obtained in preparing the concentrates which are a dark brown liquid more susceptible to reaction with the halide ion, carbon monoxide and triorganophosphorus ligand employed in forming the desired halocarbonylbis(triorganophosphorus) rhodium complex compound.

The oxidant employed for treatment of the rhodium complex concentrate may be in the form of a gas or liquid and may be selected from the class consisting of oxygen and an organic peroxide, that is to say that the oxidant can be oxygen and/or an organic peroxide. While the preferred oxidant is oxygen it is to be understood that oxygen need not be employed in its pure form, but more preferably and conveniently is employed in the form of or in admixture with an inert gas, such as nitrogen in order to minimize any explosive hazards. Indeed while oxygen in the form of air is the most preferred and convenient oxidant it too may be diluted with an inert gas such as nitrogen in order to reduce its oxygen content if operating conditions warrant such safety precautions. The liquid organic peroxides which may also be employed as oxidants herein encompass organic peroxides of the formula R—O—O—R′, wherein R represents a radical selected from the group consisting of monovalent hydrocarbon radicals of 2 to 20 carbon atoms, aroyl radicals of 7 to 20 carbon atoms, alkoxycarbonyl radicals of 2 to 20 carbon atoms and cycloalkoxycarbonyl radicals of 4 to 20 carbon atoms, and wherein R′ represents a radical selected from the group consisting of hydrogen and a radical represented by R as defined above. Preferred monovalent hydrocarbon radicals represented by R and R′ above are alkyl and aralkyl radicals, especially t-alkyl radicals of 4 to 20 carbon atoms and aralkyl radicals of 8 to 15 carbon atoms. Most preferably R′ represents hydrogen (i.e. —H). Illustrative organic peroxides include t-butylhydroperoxide, t-amylhydroperoxide, cumenehydroperoxide, ethylbenzenehydroperoxide, and the like. Such organic peroxides and/or methods for their preparation are well known in the art, the most preferred organic peroxide being t-butylhydroperoxide.

Further it is to be appreciated that the improvement in the yield of desired halocarbonylbis(triorganophosphorus) rhodium compound due to the rhodium complex concentrate's treatment with the oxidant may be accomplished by adding the oxidant to the concentrate in any manner which seems most convenient and suitable. Thus the method of treating the concentrate with the oxidant is not critical and can be accomplished simply by adding a sufficient amount of oxidant to the concentrate to obtain the desired improvement in the yield of halocarbonylbis(triorganophosphorus) rhodium compound. For instance, the gaseous or liquid oxidant can be added by carrying out the concentration of the spent hydroformylation medium in the presence of the oxidant, or during or after the concentrate is being collected. By way of example the liquid organic peroxides may be added to spent hydroformylation medium prior to the concentration procedure or to the concentrate while or after it is being collected. Likewise oxygen, and more preferably air, can be sparged into the concentrate after it has been collected, as it is being collected or while it is still a film on the walls in the thin film evaporator. The concentrate can also be agitated or stirred so as to create a vortex that will draw air from overhead into said concentrate. Alternatively spraying or atomizing the concentrate into air or allowing air to diffuse into the concentrate while or after concentration may also be employed. However because oxygen is the more preferred oxidant and because diffusion of air into the viscous concentrate can be quite slow, in order to obtain the most optimum results it is generally preferred to thoroughly disperse air throughout the concentrate, such as e.g. by directly feeding air into the concentrate after it has been collected or while it is still a film on the walls in a thin film evaporator or by agitating the concentrate and drawing air into it from overhead. Moreover it should be understood that while the oxidant treatment preferably involves directly adding the oxidant to the concentrate, if desired viscous concentrates may be first diluted with an appropriate solvent to facilitate handling prior to said oxidant treatment or with an appropriate triorganophosphorus ligand, e.g., triphenylphosphine, for storage stability prior to said oxidant treatment.

In view of the fact that the oxidant treatment encompassed herein is designed to obtain a desired improvement in the yield of halocarbonylbis(triorganophosphorus) rhodium compound over that obtained in the absence of such an oxidant treatment and because the components of the concentrate can vary both in terms of their nature and concentrations, it is apparant that no specific values can be arbitrarily given to conditions such as the amount and partial pressure (concentration) of oxidant, temperature, and contact time for the oxidant treatment. Such conditions which may vary greatly, are not narrowly critical and obviously need only be at least sufficient to obtain the improvement desired. For instance, the amount of oxidant added obviously need only be at least a sufficient amount necessary to achieve an improvement in the yield of halocarbonylbis(triorganophosphorus) rhodium compound over that obtained in the absence of such an oxidant treatment. Moreover, there appears to be no upper limit on the maximum amount of oxidant that may be employed save for it obviously not being so great as to create a hazardous explosive situation, e.g. by virtue of large concentrations or oxygen. Thus in some cases a small amount of oxidant may be more beneficial, while in other circumstances a large amount of oxidant may prove more desirable. For example, while only a small amount of oxidant may be needed in a given circumstance, it may be more desirable to use a higher concentration, and therefore a larger amount of oxidant, in order to reduce contact time. Accordingly, treatment conditions such as temperature, partial pressure (concentration) and contact time may also vary greatly depending upon among other things, the oxidant and method of treatment involved, and thus any suitable combination of such conditions may be employed herein. For instance, a decrease in any one of such conditions may be compensated for by an increase in one or both of the other conditions, while the opposite correlation is also true. In general the oxidant may be added to the concentrate at liquid temperatures ranging from 0° C. to about 250° C., while temperatures ranging from about ambient temperature to about 200° C. and more preferably from about 90° C. to about 175° C. should be suitable in most instances. Very high (greater than about 80 percent by weight) chlorocarbonylbis(triphenylphosphine) rhodium product yields have been obtained by oxidizing the concentrate with air at a temperature about 120° C. Moreover, oxygen partial pressures ranging from as little as $10^{-4}$ to 10 atmospheres should be sufficient for most purposes, while the organic peroxides can be conveniently added to the concentrate at atmospheric pressure. Of course it is obvious that the contact time will be directly related to such conditions as temperature and oxidant concentration and may vary from a matter of seconds or minutes to hours. For example, very low oxygen partial pressures and a contact time of only a matter of a few seconds may be needed when treating the concentrate with air while it exists as a thin film on the hot walls of an evaporator during the concentration procedure due to the high temperature employed in such procedures. On the other hand treating a large volume of collected concentrate with moderate oxygen partial pressures ($10^{-3}$ to 1 atmosphere) at room or ambient temperature may require a contact time of several hours or more. In general the preferred oxidative treatment will be at least sufficient to convert any remaining free triorganophosphorus ligand present in the concentrate to its corresponding triorganophosphorus oxide.

Of course it is to be understood that while it is preferred to concentrate the hydroformylation reaction medium via distillation, any suitable concentration procedure or combination of such procedures may be employed if desired. For example, free triorganophosphorus ligand present in the hydroformylation reaction medium and/or remaining in the concentrate can also be removed via the use of an alpha,beta unsaturated compound, e.g. maleic acid as taught for example in U. S. Application Ser. No. 108,279 filed Dec. 28, 1979, now U.S. Pat. No. 4,283,304, the entire disclosure of which is incorporated herein by reference thereto. In addition, while such is not necessary, if desired, the rhodium complex concentrates employable herein can be washed, both before or after oxygenation, with water, acid or a base compound prior to being employed in the subject invention.

Moreover in general as pointed out above the rhodium complex concentrate employable as the starting material of this invention consists essentially of from about 0.1 to 30 percent by weight of a spent hydroformylation reaction medium having been produced by a process comprising concentrating a spent hydroformylation reaction medium that contains a partially deactivated soluble rhodium hydroformylation catalyst, aldehyde products, higher boiling aldehyde condensation by-products and free triorganophosphorus ligand, so as to remove from said medium, while retaining a major amount of the rhodium of said catalyst present in said medium, at least essentially all, (i.e., at least about 98 percent by weight) and more preferably all of said aldehyde products present in said medium; at least about 50 percent by weight and more preferably at least about 90 percent by weight of said higher boiling aldehyde condensation by-products present in said medium having a boiling point below that of said free triorganophosphorus ligand present in said medium; and at least about 50 percent by weight and more preferably at least about 90 percent by weight of said free triorganophosphorus ligand present in said medium. Of course it is to be further understood that the process of this invention also encompasses the use of starting materials consisting essentially of blends of two or more different rhodium complex concentrates as defined herein. Further the term "essentially non-aqueous" as employed herein in relation to the homogeneous organic reaction solution of the subject process means that said solution may contain a small amount of water, but less than that amount which would destroy the basic integrity of said homogeneous solution by rendering it an aqueous-organic two phase solution. Preferably the only water present in the homogeneous organic reaction solution is that amount which might be normally associated with the possible commercial reactants employable herein.

In general the rhodium complex concentrate employable in this invention may also be considered to consist essentially of rhodium and preferably 0 to about 10 percent by weight of free triorganophosphorus ligand based on the total weight of the concentrate, the remainder of said concentrate consisting essentially of higher boiling aldehyde condensation by-products and phosphorus oxides, said condensation by-products and oxides having generally been produced in situ during the hydroformylation process and/or by said above oxidative treatment of the concentrate. The most preferred rhodium complex concentrate starting materials of this invention are oxygenated rhodium complex concentrates as explained above which are devoid of any said aldehyde products and free triorganophosphorus ligand, any remaining free triorganophosphorus ligand present in the non-oxygenated concentrate having been converted to its corresponding triorganophosphorus oxide by the oxygenation of the concentrate as explained above.

The second main component of the essentially non-aqueous homogeneous organic reaction solution of this invention is a halide ion source. Any suitable halide ion source may be employed in the present invention which will furnish the halogen radical of the desired halocarbonylbis(triorganophosphorus) rhodium product. Such halogen radicals include, of course, chlorine, bromine, iodine and fluorine with chlorine being preferred. Illustrative sources of such halide ions include halogens, halohydric acids, halide salts e.g., alkali metal halides and the like; for instance, hydrochloric acid, hydrobromic acid, hydroiodic acid, sodium chloride, sodium bromide, and the like. The preferred source of halide ion is a hydrohalic acid especially hydrochloric acid. Of course it is obvious that the source of halide ion need only be employed in an amount sufficient to provide at least that stoichiometric amount of halogen ion necessary to form the desired halocarbonylbis(triorganophosphorus) rhodium product, i.e., at least one mole equivalent of halogen ion per mole of rhodium calculated as free metal in the rhodium complex concentrate starting material. In general, it is preferred to employ a molar excess of halogen ion. Thus while the upper limit of the amount of halogen ion employed is not critical, it is generally preferred to employ that amount of halogen ion source which will provide amounts ranging from about 1 to about 6 mole equivalents, and more preferably from about 2 to about 5 mole equivalents of halogen ion per mole of said rhodium present in the rhodium complex concentrate starting material. Of course it is to be understood that since the preferred hydrohalic acids employed are conventional concentrated aqueous containing acids the amount of hydrohalic acid employed should not be so large that the amount of water contained therein would create a non-homogeneous, two-phase mixture when combined with the other reactants of the process of this invention.

The third main component of the essentially non-aqueous homogeneous organic reaction solution of this invention is carbon monoxide gas or a carbon monoxide source. Any suitable carbon monoxide source, as an alternative to carbon monoxide gas per se, may be employed in the present invention which will furnish the carbonyl radical of the desired halocarbonylbis(triorganophosphorus) rhodium product. Illustrative sources of carbon monoxide include any organic compound containing an aliphatic carbon to oxygen bond which in the process of this invention will provide the carbonyl radical complexed to the rhodium of the desired product, for example, aldehydes such as formaldehyde, acetaldehyde, benzaldehyde, and the like; alcohols such as ethanol, allyl alcohol, benzyl alcohol and the like; amides such a N,N-dimethylformamide, N,N-dimethylacetamide, formanilide, and the like; carboxylic acids such as formic acid, and the like; esters such as ethyl formate, ethyl acetate, benzyl formate, diethyl carbonate, and the like; acid chlorides such as acetyl chloride, benzoyl chloride, phosgene, ethylchloroformate, and the like; ethers such a p-dioxane, propylene oxide, and the like; as well as other such types of compounds providing that they are not adversely detrimental to the purpose of this invention. In general, it is preferred to employ a source of carbon monoxide rather than carbon monoxide gas per se. The preferred source of carbon monoxide are high boiling amides, especially N,N-dimethylformamide, since such has been found to not only serve as a source of carbon monoxide, but also as an excellent solvent and/or compatibilizing agent for rendering the preferred hydrochloric acid and triphenylphosphine components of the process of this invention completely homogeneous with the rhodium complex concentrate employed in the process of this invention. Of course it is obvious that the source of carbon monoxide need only be employed in an amount sufficient to provide at least that stoichiometric amount of carbon monoxide necessary to form the desired halocarbonylbis(triorganophosphorus) rhodium product, i.e., at least one mole equivalent of carbon monoxide per mole of rhodium calculated as free metal in the rhodium complex starting material. The same stoichiometric ratio is of course necessary if one employs carbon monoxide gas per se. In general it is preferred to employ a molar excess of carbon monoxide. Thus while the upper limit of the amount of carbon monoxide employed is not critical, it is generally preferred to employ that amount of carbon monoxide gas or carbon monoxide source which will provide amounts ranging from about 1 to 500 mole equivalents and more preferably from about 20 to 100 mole equivalents of carbon monoxide per mole of said rhodium present in the rhodium complex concentrate starting material. Of course it is to be understood that the amount of carbon monoxide gas or carbon monoxide source employed should not be so large as to be highly adversely detrimental to the yield of desired halocarbonylbis(triorganophosphorus) rhodium product. In the most preferred aspect of this invention from about 20 to about 50 parts by volume of N,N-dimethylformamide per 100 parts by volume of rhodium complex concentrate employed should be sufficient in most instances.

The fourth main component of the essentially non-aqueous homogeneous organic reaction solution of this invention is a free triorganophosphorus ligand (i.e., ligand that is not complexed with or tied to the rhodium of the partially deactivated rhodium complex catalyst). Any suitable free triorganophosphorus ligand may be employed in the present invention to furnish the triorganophosphorus radicals of the desired halocarbonylbis(triorganophosphorus) rhodium complex. Obviously the choice of such phosphorus ligands will merely depend upon the nature of the rhodium complex product desired. Such phosphorus ligands are well known and include those already discussed above. For example in general, the preferred phosphorus ligands are those which have been heretofore employed as rhodium ligands in the hydroformylation field, e.g., as seen by U.S. Pat. No. 3,527,809. Illustrative free triorganophosphorus ligands that may be employed in the present include, e.g., triorganophosphines, triorganophosphites, triorganophosphinites, triorganophosphonites, and the like, in which the organic radicals are the same or different. Illustrative organic radicals include, e.g., alkyl, aryl, aralkyl, alkaryl and cycloalkyl radicals containing from 1 to 20 carbon atoms, which radicals may further contain groups or substituents, if desired, such as halogen, alkoxy, aryloxy, and the like, which do not essentially interfere with the course of the novel process of this invention. Preferably the triorganophosphorus ligand employed herein is a triorganophosphine, and more preferably a triarylphosphine, especially triphenylphosphine. The amount of free triorganophosphorus ligand employed need only be at least that stoichiometric amount necessary to form the desired halocarbonylbis(triorganophosphorus) rhodium product, i.e., at least two mole equivalents of free triorganophosphorus ligand per mole of rhodium calculated as free metal in the rhodium complex concentrate starting material. In general, it is preferred to employ a molar excess of free triorganophosphorus ligand. While the upper limit of the amount of free triorganophosphorus ligand employed is not critical, amounts ranging from about 2 to about 50 mole equivalents, and more preferably from about 4 to about 20 mole equivalents of free triorganophosphorus ligand per mole of said rhodium in the rhodium complex concentrate starting material should be sufficient in most instances. Moreover, it is to be understood that while it is generally preferred to form the homogeneous organic reaction solution employed in this invention with a deliberate charge of said free triorganophosphorus ligand, if the rhodium complex concentrate employed already contains free triorganophosphorus ligand, the amount of such free triorganophosphorus ligand charged may be reduced if desired by that amount already contained in said concentrate. Indeed in some instances if said concentrate contains sufficient free triorganophosphorus ligand it may not even be necessary to employ such a deliberate charge of triorganophosphorus ligand.

Moreover, if desired, any suitable polar protic or dipolar aprotic organic solvent or mixtures of such solvents can be employed as an additional component for the purpose of rendering the essential components of the process of this invention miscible with each other and to help maintain the integrity of the novel organic one-phase, homogeneous system of the process of this invention. Illustrative typical solvents which may be employed include, for example, alcohols such as ethanol, isopropanol, and the like; ethers such as 1,2-dimethoxyethane, p-dioxane, and the like. Of course it is to be understood that the use of such solvents as an additional component to the process of this invention is not absolutely necessary and is normally not even desired when the essential components employed in the process of this invention are completely compatible with each other. For example, in the most preferred aspect of this invention the presence of an organic solvent as an additional component to the process is not necessary or desired, since the preferred source of carbon monoxide, e.g. N,N-dimethylformamide, also serves to provide the desired effect of a dipolar aprotic solvent. However, such organic solvents can be helpful in increasing the yield of desired product when the essential components employed in the process of this invention are not so completely compatible with each other. Thus, the amount of any such solvent when employed will merely depend upon the nature of the solvent and the nature and amounts of the various essential components of the process of this invention and may obviously vary from case to case. However, the preferred amount of such solvent can easily be determined by simple routine experimentation. In addition to helping maintain the integrity of the novel organic one-phase, homogeneous system of the process of this invention, the proferred organic solvent when employed should also, of course, be one in which the desired halocarbonylbis(triorganophosphorus) rhodium product has a low solubility.

As pointed out above the process of this invention comprises reacting at a temperature of from about 40° to about 200° C. and more particularly from about 130° C. to about 190° C., an essentially non-aqueous, homogeneous organic reaction solution consisting essentially of (a) a rhodium complex concentrate, (b) a halide ion source, (c) carbon monoxide gas or a carbon monoxide source and (d) free triorganophosphorus ligand for at least a sufficient period of time to form the desired halocarbonylbis(triorganophosphorus) rhodium compound, i.e. HalRh(CO)(PX$_3$)$_2$ wherein Hal is halogen and PX$_3$ is a triorganophosphorus radical. The most preferred aspect of this invention comprises heating said essentially non-aqueous, homogeneous organic reaction solution to reflux and refluxing said solution at least until the desired halocarbonylbis(triorganphosphorus) rhodium compound is formed. Formation of the desired halocarbonylbis(triorganophosphorus) rhodium product and completion of the reaction can be readily determined and monitored by any suitable conventional method e.g. such as by atomic absorption analysis of aliquot samples of the reaction solution during the process to determine the amount of rhodium calculated as free metal remaining and/or by infrared spectrometry or nuclear magnetic resonance analysis to determine the presence of desired product. Completion of the reaction is evidenced by a constant amount of said rhodium being found in successive aliquot samples of the reaction solution taken to monitor to the process. Of course it is to be understood that the particular desired reaction temperature and reaction time with regard to a given process will depend upon such obvious factors as the nature and amounts of the reactive components employed, the amount of product desired, and the like. In general, the reaction process of this invention is preferably conducted at least until a suspension of the desired product is formed in the reaction solution (i.e. mother liquor) as evidenced by the appearance of a precipitate of the desired halocarbonylbis(triorganophosphorus) rhodium compound in said solution, and of course most preferably until the reaction is completed, which should normally take several hours.

Moreover the reaction process of this invention may be conducted in any suitable reaction vessel and the reactive organic solution formed merely by combining the essential reactive components of the process in any order desired. In general it is preferred to add the carbon monoxide source and triorganophosphorus ligand to the rhodium complex concentrate followed by the halide ion source. Moreover, the process of this invention is preferably conduced in the presence of air and under atmospheric conditions, i.e., at about 1 atmosphere. However, it is to be understood that the exact pressure is not critical and may range from about 1 atmosphere or lower to about 35 atmospheres or higher and that the process can be conducted in an inert gas atmosphere, if desired.

The solid crystalline and sparingly soluble complex of halocarbonylbis(triorganophosphorus) rhodium product precipitate may be isolated and recovered if desired by any suitable conventional method, e.g. such as by filtration at room temperature, and the like. Moreover, if desired any suitable solvent e.g. an alcohol such as methanol, ethanol, isopropanol, and the like, may be employed in the recovery procedure to further desolubilize the desired halocarbonylbis(triorganophosphorus) rhodium compound and increase the recovery of the yield of desired product precipitates. Of course repeating the subject process of this invention, if desired, using the filtrate or mother liquor of the initial process as the starting material may also increase the total yield of desired product.

The subject process of this invention is indeed unique and provides numerous advantages over heretofore prior art methods. For instance, the subject process involves an organic one-phase reaction, i.e. a reaction that does not require or involve transfer of the rhodium values from one liquid phase to another during the reaction, and thus avoids such disadvantages as handling problems and costly rhodium losses that can accompany prior art liquid phase transfer type process. In addition due to the relatively small volume or organic liquids that would be required in the subject process to convert a given amount of rhodium values to said halocarbonylbis(triorganophosphorus) rhodium compounds as compared to the much larger volume of organic liquids and water that would be required by an aqueous phase transfer type process to produce the same amount of desired product from said given amount of rhodium values, it is obvious that the subject invention has the technical advantage over such processes of being able to process such amounts of rhodium values in a much smaller and less expensive reaction vessel, or for equipment of fixed size, to produce more of the desired product in a given period of time. Moreover, the subject process does not possess the environmental and by-product disposal problems that can be attendant with aqueous phase transfer type processes. For example, undesirable by-products of the subject process can easily be disposed of by burning whereas contaminated water must or at least should undergo a water purification treatment before it can be reused or discarded.

More specifically since the subject process of this invention has the distinct advantage of being able to employ starting materials which contain very large amounts of rhodium values and to convert those rhodium values in a simple manner and in a single reaction vessel into high yields of said halocarbonylbis(triorganophosphorus) rhodium compounds, the subject process provides an excellent method for recovering the intrinsically deactivated rhodium values of large scale commercial hydroformylation operations as explained above. For reasons not completely understood such deactivated rhodium values are not as easily converted into halocarbonylbis(triorganophosphorus) rhodium, as are for example simple rhodium type monomers and it is believed that the more deactivated such rhodium values are, the more difficult the conversion. However high yields of desired product have been able to be obtained by the subject process of this invention even when the rhodium values are derived from a rhodium complex hydroformylation catalyst that has been employed in a hydroformylation process for a sufficient period of time to become even more than 60 percent deactivated.

The subject process for preparing halocarbonylbis(triorganophosphorus) rhodium compounds is also considered unique in that it produces the desired halo-containing rhodium compounds in such a fashion that it is not even necessary to isolate said halo-containing compounds from their product mother liquor prior to being useful starting materials for the production of hydridocarbonyltris(triorganophosphorus) rhodium compounds as explained more fully below.

The halocarbonylbis(triorganophosphorus) rhodium products of this invention have a wide range of utility well known in the art. For example they can be employed directly as catalysts in hydrogenation reactions such as in the production of alkanes from olefins and in the production of alcohols from aldehydes, and as catalysts and/or catalytic precursors in hydroformylation reactions to produce aldehydes from olefins. Alternatively such halocarbonylbis(triorganophosphorus) rhodium compounds can be converted to hydridocarbonyltris(triorganophosphorus) rhodium compounds by any suitable conventional method known in the art. Such hydridocarbonyltris(triorganophosphorus) rhodium compounds, i.e. $HRh(CO)(PX_3)_3$ wherein $PX_3$ is a triorganophosphorus radical, also have a wide range of utility well known in the art, e.g. they are especially suitable for employment in low pressure oxo hydroformylation reactions designed to hydroformylate olefins and produce aldehyde products rich in their normal isomers.

As pointed out above another aspect of this invention relates to a process for preparing a hydridocarbonyltris(triorganophosphorus) rhodium compound which comprises reacting at a temperature of from about 20° C. to about 100° C. and more preferably from about 25° C. to about 80° C., a halocarbonylbis(triorganophosphorus) rhodium compound produced according to the process of this invention as outlined above, without isolating said halocarbonylbis(triorganophosphorus) rhodium compound from its product solution (mother liquor), with a metal hydride reducing agent and free triorganophosphorus ligand for at least a sufficient period of time to form said hydridocarbonyltris(triorganophosphorus) rhodium compound.

Of course it is obvious that any halocarbonylbis(triorganophosphorus) rhodium compound prepared according to the process of this invention as described above and which has not been isolated from its product solution can be employed as the starting material for preparing the desired hydridocarbonyltris(triorganophosphorus) rhodium compound. Thus it is also to be understood that the preferred embodiments for preparing such halocarbonylbis(triorganophosphorus) rhodium compounds as discussed above are also correspondingly the preferred embodiments that will lead to the preferred halocarbonylbis(triorganophosphorus) containing starting materials employable in producing said hydridocarbonyltris(triorganophosphorus) rhodium compounds. The most preferred starting materials are those containing $ClRh(CO)(P\phi_3)_2$ such that the desired product produced in $HRh(CO)(P\phi_3)_3$, wherein $\phi$ in said formulas represents a phenyl radical.

Any suitable metal hydride reducing agent may be employed in the subject process which will supply the necessary hydrogen of the desired hydridocarbonyltris(triorganophosphorus) rhodium products. Illustrative hydrides include alkali metal and alkali earth metal borohydrides or aluminumhydrides, such as sodium borohydride, sodium cyanoborohydride, sodium trimethoxyborohydride, Vitride®, and the like. The most preferred hydride is sodium borohydride [$NaBH_4$]. In general the amount of metal hydride employed is not critical and need only be at least sufficient to produce the desired hydridocarbonyl-containing rhodium product and thus may range from about 1 to about 25 mole equivalents or higher, and more preferably from about 5 to about 20 mole equivalents of metal hydride per mole of rhodium calculated as free metal in the halocarbonylbis(triorganophosphorus) rhodium containing starting material. Most preferably about 10 mole equivalents of sodium borohydride are employed per mole of said rhodium.

Moreover it is generally preferred to employ an organic solvent solution of said metal borohydrides and any suitable organic solvent for the metal borohydride which does not unduly adversely affect the desired process reaction and in which the desired hydridocarbonyltris-(triorganophosphorus) rhodium product has a low solubility may be employed. Typical organic solvents include e.g., alcohols such as ethanols, isopropanol, and the like, and amides such as N,N-dimethylformamide, and the like. The most preferred solvent for the sodium borohydride is N,N-dimethylformamide. The amount of solvent employed obviously need only preferably be at least that amount sufficient to solubilize the metal borohydride employed.

The amount of free triorganophosphorus ligand present during the subject reduction process to the desired hydrido containing rhodium complex need only be at least that amount necessary to provide the third triorganophosphorus radical of the desired hydridocarbonyltris(triorganophosphorus) rhodium product. Preferably an excess amount of such free triorganophosphorus ligand is present during the subject reduction process. While the upper limit of the amount of free triorganophosphorus ligand present is not critical, amounts ranging from about 3 to about 50 mole equivalents, and more preferably from about 5 to 20 mole equivalents of free triorganophosphorus ligand per mole of rhodium calculated as free metal present in the halocarbonylbis(triorganophosphorus) rhodium-containing starting material should be sufficient for most purposes. Moreover, it is to be understood that if the halocarbonylbis(triorganophosphorus) rhodium containing starting material already contains sufficient free triorganophosphorus ligand to provide the third triorganophosphorus radical of the desired hydridocarbonyltris(triorganophosphorus) rhodium product it may not be absolutely necessary to deliberately add any additional free triorganophosphorus ligand to said starting material. The free triorganophosphorus ligand can of course be any of such phosphorus ligands as herein fully discussed above. The most preferred ligand is again triphenylphosphine.

While not absolutely critical to the subject reduction process of this invention it is further generally preferred to carry out the reduction process in the presence of an organic diluent which can help provide a suitable compatible medium for the reactants involved. While any suitable organic diluent may be employed which would not unduly adversely affect the subject process, it is preferred to employ an organic diluent in which both the precipitated halocarbonylbis(triorganophosphorus) rhodium starting material and the desired hydridocarbonyltris(triorganophosphorus) rhodium precipitated product are highly insoluble so as to decrease the solubility of both said rhodium precipitates in their respective liquids thereby helping to insure recovery of the most optimum yield of desired hydrido-containing rhodium complex product possible. Thus in general the preferred organic diluents are aliphatic alcohols containing from 2 to 5 carbon atoms such as ethanol, isopropanol, and the like, especially isopropanol. While the amount of organic diluent employed is obviously not critical, when employed amounts ranging from about 50 to about 200 parts by volume of organic diluent per 100 parts of volume of the halocarbonylbis(triorganophosphorus) rhodium containing starting material should be sufficient in most instances. More preferably about equal volumes of said organic diluent and said starting material are generally employed.

Of course the reduction process of this invention may be carried out in any suitable manner. In general it is preferably conducted by cooling the halocarbonylbis(triorganophosphorus) rhodium containing product mixture so produced according to this invention as outlined above, adding at about room temperature, that amount of desired organic diluent and/or free triorganophosphorus ligand followed by the desired amount of solubilized metal hydride and then refluxing, while stirring, the reaction mixture, most preferably at about 60° C., for at least a sufficient period of time to form the desired hydrido-containing rhodium complex compound. Formation of the desired hydridocarbonyltris(triorganophosphorus) rhodium product is evidenced by the formation of a new precipitate after the disappearance of the solid halocarbonylbis(triorganophosphorus) rhodium into the reaction solution during the reaction. The reaction is very rapid and generally can be completed within a matter of minutes or only a couple of hours depending upon such obvious factors as the amount of reactants employed, and the like. Completion of the reaction and identification of the desired hydrido-containing rhodium complex can be confirmed by any suitable conventional method. Moreover for safety considerations it is recommended to conduct the subject reduction process in an inert gas atmosphere, e.g., nitrogen, and the like. The exact pressure is not critical and any suitable pressure conditions may be employed.

Of course it is further obvious that the subject reduction process can be carried out in the same reaction vessel employed in preparing the halocarbonylbis(triorganophosphorus) rhodium compound or in any other suitable reaction vessel as desired. Likewise the desired hydridocarbonyltris(triorganophosphorus) rhodium precipitate may be recovered from its product mixture by any suitable manner. However the preferred method for recovering said hydrido-containing rhodium precipitate in high yields is to employ a solid bowl centrifuge, such as a Sharples P-600D Super-D-Canter. The recovered wet solids can then be washed, if desired, and dried. It is further generally preferred to add an aqueous alcoholic solution, such as aqueous isopropanol, to the precipitated hydrido-containing rhodium product mixture so as to further desolubilize the desired hydridocarbonyltris(triorganophosphorus) rhodium compound prior to centrifuging it as explained above.

As noted above the subject reduction process of this invention is indeed unique in that it involves a novel method for preparing high yields of hydridocarbonyltris(triorganophosphorus) rhodium compounds from halocarbonylbis(triorganophosphorus) rhodium compounds without ever having to isolate said halo-containing rhodium compounds from the mother liquor in which they are produced.

The following examples are illustrative of the present invention and are not to be regarded as limitative. It is to be understood that all of the parts, percentages and proportions referred to herein and the appended claims are by weight unless otherwise indicated, the given amounts of rhodium being calculated as free metal. The symbol $\phi$ in the formulas represents a phenyl radical.

EXAMPLE 1

A spent hydroformylation reaction medium obtained from a continuous hydroformylation process of propylene with carbon monoxide and hydrogen to produce butyraldehyde in the presence of a rhodium complex catalyst consisting essentially of rhodium complex with carbon monoxide and triphenylphosphine, and free triphenylphosphine, said medium containing less than 400 ppm rhodium, and whose catalytic activity had declined to about 30 percent of that of fresh catalyst was concentrated in a thin-film evaporator to remove by distillation, while retaining essentially all of the rhodium of said catalyst, all of the butyraldehyde products present in said medium, more than 90 percent by weight of the aldehyde condensation by products present in said medium that have a boiling point below that of said free triphenylphosphine ligand present in said medium, and more than 90 percent by weight of said free triorganophosphine ligand present in said medium, and produce a highly viscous rhodium complex concentrate distillation residue consisting essentially of less than about 5 percent by weight of said medium and containing about 8000 ppm rhodium and a minor amount of free triphenylphosphine ligand (about 2.7 percent by weight based on the total weight of said concentrate), the remainder of said concentrate consisting essentially of higher boiling aldehyde condensation by-products (more than 35 percent by weight of said condensation by-products having a boiling point above that of said free triphenylphosphine ligand) and phosphine oxide. About 675 grams of said rhodium complex concentrate was then oxygenated with air at about 90° C. for about 24 hours (said oxidative treatment being sufficient to convert all free phosphine ligand present in said concentrate to its corresponding phosphine oxide).

The 675 grams of said oxygenated rhodium complex concentrate (analyzed to contain about 5.55 grams of rhodium) was then added along with about 200 ml. (about 34 mole equivalents based on said amount of rhodium) of N,N-dimethylformamide, about 70.8 grams (about 5 mole equivalents based on said amount of rhodium) of triphenylphosphine and about 13 ml. (about 3 mole equivalents based on said amount of rhodium) of concentrated hydrochloric acid to a three-necked flask equipped with a magnetic stirring bar, a thermometer and a reflux condensor to form an essentially non-aqueous, homogeneous organic reaction solution which was heated to reflux and refluxed with stirring overnight (about 149° C. to about 180° C.) in the presence of air (about 1 atmosphere) to form a brownish suspension of precipitated ClRh(CO) (P$\phi_3$)$_2$ in the mother liquor of the process. After cooling to room temperature said suspension was diluted with about one liter of methanol and then filtered to obtain said desired ClRh(CO) (P$\phi_3$)$_2$ solids which had a greenish color. The amount of rhodium remaining in the filtrate was determined by atomic absorption to be about 34 percent by weight of that contained in the oxygenated concentrate starting material. The amount of rhodium recovered as solid ClRh(CO) (P$\phi_3$)$_2$ thus corresponding to a yield of about 66 percent. Elemental analysis, infrared spectrometry and $^{31}$P nuclear magnetic resonance analysis confirm that the recovered solid product was indeed chlorocarbonylbis(triphenylphosphine) rhodium as shown by the above formula.

EXAMPLES 2 TO 6

A series of 100 gram samples of the rhodium complex concentrate produced as described in Example 1 were oxygenated with air as set forth in the Table below. The air treatments employed in each instance were sufficient to convert all of the free phosphine ligand present in the concentrate to its corresponding phosphine oxide.

Said 100 gram oxygenated concentrate samples (each analyzed to contain about 0.81 grams of rhodium) where then mixed with about 3 mole equivalents of various concentrated hydrohalic acids (see the Table below) based on said amount of rhodium, about 5 mole equivalents of free triphenylphosphine ligand based on said amount of rhodium and about 35 ml. of N,N-dimethylformamide and the reaction solution refluxed overnight (about 149° C. to about 180° C.) as described in Example 1. The amount of rhodium recovered as solid HalRh(CO)(P$\phi_3$)$_2$, said product being confirmed in each instance by infrared spectrometry is given in the following Table.

TABLE

| Ex. No. | Concentrated Acid | Air Treatment Temp. | Hours | % Rhodium Recovered |
|---|---|---|---|---|
| 2 | Hydrochloric | 120° C. | 24 | 89 |
| 3 | Hydrobromic | 120° C. | 24 | 87.5 |
| 4 | Hydroiodic | 120° C. | 24 | 85.7 |
| 5 | Hydrochloric | 90° C. | 24 | 70 |
| 6 | Hydrochloric | NONE | | 35 |

EXAMPLE 7

Another 100 gram sample of the rhodium complex concentrate produced as described in Example 1 was oxygenated with air at about 120° C. for 24 hours. Said air treatment was sufficient to convert all of the free phosphine ligand present in the concentrate to its corresponding phosphine oxide.

Said 100 gram oxygenated concentrate sample (analyzed to contain about 0.77 grams of rhodium) was mixed with about 3 mole equivalents of concentrated hydrochloric acid based on said amount of rhodium, about 5 mole equivalents of free triphenylphosphine ligand based on said amount of rhodium and about 35 ml. of N,N-dimethylacetamide and the reaction solution refluxed overnight at about 140° C. as described in Example 1. The amount of rhodium recovered as solid ClRh(CO)(P$\phi_3$)$_2$, said product being confirmed by infrared spectrometry, corresponded to about a 69 percent yield.

EXAMPLE 8

Another 100 gram sample of the rhodium complex concentrate produced as described in Example 1 was oxygenated with air at about 120° C. for 24 hours. Said air treatment was sufficient to convert all of the free phosphine ligand present in the concentrate to its corresponding phosphine oxide.

Said 100 gram oxygenated concentrate sample (analyzed to contain about 0.76 grams of rhodium) was then mixed with about 46.5 ml of diethylamine, about 5 mole equivalents of free triphenylphosphine based on said amount of rhodium and about 3 moles of concentrated hydrochloric acid based on said amount of rhodium and the reaction solution stirred and heated overnight at about 90° C. under an atmosphere of carbon monoxide gas to form a suspension of precipitated ClRh(CO)(P$\phi_3$)$_2$ in the mother liquor of the process. After cooling to room temperature said suspension was diluted with about 200 ml. of methanol and then filtered. The amount of rhodium recovered as solid ClRh(CO)(P$\phi_3$)$_2$, said product being confirmed by infrared spectrometry, corresponded to about a 72.4 percent yield.

EXAMPLE 9

Another 100 gram sample of the rhodium complex concentrate produced as described in Example 1 was oxygenated at 120° C. with air overnight, said oxidative treatment being sufficient to convert all the free phosphine ligand in said concentrate to its corresponding phosphine oxide.

Said 100 gram oxygenated rhodium complex concentrate (analyzed as containing about 0.79 grams of rhodium) was charged along with about 35 ml. of N,N-dimethylformamide, about 5 mole equivalents of free triphenylphosphine ligand based on said amount of rhodium, and about 3 mole equivalents of concentrated hydrochloric acid to a three neck flask equipped with a thermometer, magnetic stirring bar and reflux condensor. The reaction solution was then heated to reflux and refluxed overnight (about 149° C. to about 180° C.) in air (about 1 atmosphere) to form a suspension of precipitated ClRh(CO)(P$\phi_3$)$_2$ product in the mother liquor. Said suspension was then cooled and diluted with about 100 ml. of ethanol to further desolubilize said precipitate. The diluted suspension, without isolating the precipitate therefrom, was then heated to reflux and a solution of about 3.2 grams of sodium borohydride in 200 ml. of ethanol added over a 15 minute period and the reaction solution refluxed for an additional 15 minutes to produce a precipitated suspension of desired HRhCO(P$\phi_3$)$_3$ product. After cooling yellow-greenish solids of said desired HRhCO(P$\phi_3$)$_3$ product were obtained by filtration and about 366 grams of filtrate recovered. The amount of rhodium remaining in said filtrate was found to be about 0.09 grams or about 11.4 percent by weight of that contained in the oxygenated concentrate starting material. The amount of rhodium recovered as HRh(CO)(P$\phi_3$)$_3$ thus corresponds to a yield of about 88.6 percent. Infrared spectrometry confirmed that the recovered solid product was indeed hydridocarbonyltris(triphenylphosphine) rhodium as shown by the above formula.

EXAMPLE 10

An essentially non-aqueous, homogeneous organic reaction solution containing about 5.13 grams of a rhodium complex concentrate distillation residue of a spent hydroformylation reaction medium (said concentrate containing about 14,200 ppm rhodium), about 10 ml. of anhydrous ethanol, and about 0.47 ml. of concentrated hydroiodic acid was heated at 90° C. under one atmosphere of carbon monoxide gas for 17 hours. Then about 1.86 grams of triphenylphosphine and another 20 ml. of ethanol were added to the solution. This solution was also heated at 90° C. under one atmosphere of carbon monoxide for about 3.5 hours to form a suspension of precipitated IRh(CO)(P$\phi_3$)$_2$ in the mother liquor. The amount of rhodium recovered as precipitated product corresponded to about a 56 percent yield and the formation of iodocarbonylbis(triphenylphosphine) rhodium was confirmed by infrared analysis.

Various modifications and variations of this invention will be obvious to a worker skilled in the art and it is to be understood that such modifications and variations are to be included within the purview of this application and the spirit and scope of the appended claims.

What is claimed is:

1. An organic one-phase process for preparing a halocarbonylbis(triorganophosphorus) rhodium compound which comprises reacting, at a temperature from about 20° C. to about 200° C., an essentially non-aqueous homogeneous organic reaction solution consisting essentially of (a) a rhodium complex concentrate, (b) a halide ion source, (c) carbon monoxide gas or a carbon monoxide source and (d) free triorganophosphorus ligand, for at least a sufficient period of time to form said halocarbonylbis(triorganophosphorus) rhodium compound; said rhodium complex concentrate consisting essentially of from about 0.1 to about 30 percent by weight of a spent hydroformylation reaction medium and having been produced by concentrating a spent hydroformylation reaction medium that contains a partially deactivated soluble rhodium complex hydroformylation catalyst, aldehyde products, higher boiling aldehyde condensation by-products, and free triorganophosphorus ligand, so as to remove from said medium, while retaining a major amount of the rhodium values of said catalyst present in said medium, at least essentially all of said aldehyde products, at least 50 percent by weight of said higher boiling aldehyde condensation by-products that have a boiling point below that of said free triorganophosphorus ligand present in said medium and at least 50 percent by weight of said free triorganophosphorus ligand present in said medium.

2. A process as defined in claim 1, wherein the rhodium complex concentrate consists essentially of from about 1 to 10 percent by weight of said spent hydroformylation reaction medium.

3. A process as defined in claim 2, wherein said concentrate has been oxygenated, the oxidative treatment being at least sufficient to convert any remaining free triorganophosphorus ligand present in the concentrate to its corresponding triorganophosphorus oxide.

4. A process as defined in claim 3, wherein the oxidative treatment is conducted at a temperature of about 90° to about 175° C.

5. A process as defined in claim 4, wherein the oxidative agent is air.

6. A process as defined in claim 4, wherein said halide ion source is a hydrohalic acid.

7. A process as defined in claim 6, wherein said acid is hydrochloric acid.

8. A process as defined in claim 4, wherein carbon monoxide gas is employed.

9. A process as defined in claim 4, wherein a carbon monoxide source is employed.

10. A process as defined in claim 9, wherein the carbon monoxide source is an amide and wherein the reaction temperature ranges from about 130° C. to about 190° C.

11. A process as defined in claim 10, wherein said amide is N,N-dimethylformamide.

12. A process as defined in claim 4, wherein said free triorganophosphorus ligand is triphenylphosphine.

13. A process as defined in claim 4, wherein a suspension of precipitated chlorocarbonylbis(triorganophosphine) rhodium is prepared by refluxing the essentially non-aqueous, homogeneous reaction solution, at a temperature of from about 130° C. to about 190° C. consisting essentially of (a) said oxygenated rhodium complex concentrate, (b) hydrochloric acid, (c) N,N-dimethylformamide and (d) free triphenylphosphine ligand.

14. A process as defined in claim 13, wherein the oxidative agent is air.

15. A process as defined in claim 14, wherein the chlorocarbonylbis(triphenylphosphine) rhodium compound is isolated and recovered from said suspension.

16. A process for preparing a hydridocarbonyltris(triorganophosphorus) rhodium compound which comprises reacting, at a temperature of from about 20° C. to about 100° C., the halocarbonylbis(triorganophosphorus) rhodium compound produced as defined in claim 1 without isolating said halocarbonylbis(triorganophosphorus) rhodium compound from its product mixture, with a metal hydride reducing agent and free triorganophosphorus ligand, for at least a sufficiet period of time to form said hydridocarbonyltris(triorganophosphorus) rhodium compound.

17. A process as defined in claim 16, wherein said metal hydride is a borohydride and said free triorganophosphorus ligand is triphenylphosphine.

18. A process for preparing hydridocarbonyltris(triphenylphosphine) rhodium which comprises reacting at a temperature of from about 20° C. to about 100° C., the chlorocarbonylbis(triphenylphosphine) rhodium compound produced as defined in claim 13, without isolating said chlorocarbonylbis(triphenylphosphine) rhodium compound from its product mixture, with a metal borohydride reducing agent and free triphenylphosphine for at least a suffient period of time to form said hydridocarbonyltris(triphenylphosphine) rhodium compound.

19. A process as defined in claim 18, wherein the metal borohydride is sodium borohydride and wherein the reduction process is conducted in the presence of an aliphatic alcohol containing from 2 to 5 carbon atoms.

20. A process as defined in claim 19, wherein the oxidant employed in oxygenating the rhodium complex concentrate is air, wherein the aliphatic alcohol is ethanol and isopropanol and wherein a solvent solution of said sodium borohydride is employed.

* * * * *